US00PP14726P3

(12) United States Plant Patent
Moser

(10) Patent No.: US PP14,726 P3
(45) Date of Patent: Apr. 20, 2004

(54) CHRYSANTHEMUM PLANT NAMED 'MOZA SUNC 02'

(50) Latin Name: *Dendranthema morifolium*
Varietal Denomination: Moza Sunc 02

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 0 days.

(21) Appl. No.: 10/136,814

(22) Filed: Apr. 30, 2002

(65) Prior Publication Data

US 2003/0204890 P1 Oct. 30, 2003

(51) Int. Cl.[7] ..... A01H 5/00
(52) U.S. Cl. ..... Plt./295
(58) Field of Search ..... Plt./295

(56) References Cited

U.S. PATENT DOCUMENTS

PP11,238 P 2/2000 Pieters ..... Plt./295

OTHER PUBLICATIONS

Chrysanthemum once again Horticulture Science Dick Brummitt.*

* cited by examiner

*Primary Examiner*—Bruce R. Campell
*Assistant Examiner*—Annette H Para
(74) *Attorney, Agent, or Firm*—Knobbe, Martens, Olson & Bear, LLP

(57) ABSTRACT

A new and distinct Chrysanthemum plant cultivar is disclosed, characterized by a daisy-type inflorescence, consistent flowering response to short days, blooming consistently after 49 days of short day length, free branching habit, yellow ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Dendranthema morifolium.*

Variety denomination: The new and distinct Chrysanthemum plant is hereinafter referred to by the cultivar name 'Moza Sunc 02.'

BACKGROUND OF THE INVENTION

The new cultivar is a product of hybridization of a female parent Chrysanthemum plant variety 'MZ-923' (undistributed in the United States) and a male parent Chrysanthemum plant variety 'MZ-617' (undistributed in the United States). The new cultivar was discovered and selected by the inventor in October 1999.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Moza Sunc 02' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Moza Sunc 02.' These characteristics in combination distinguish 'Moza Sunc 02' as a new and distinct Chrysanthemum cultivar:

1. Daisy-type inflorescence,
2. Consistent flowering response to short days, blooming consistently after 49 days of short day length, 3. Free branching habit,
4. Yellow ray florets,
5. Very uniform round growth habit, and
6. Large quantity of blooms per flowering branch.

Plants of the new cultivar are similar to plants of the female parent variety, 'MZ-923' in most horticultural characteristics, however plants of the new cultivar have differently colored ray florets, more ray florets per inflorescence, and a more persistent inflorescence than plants of the female parent variety.

Plants of the new cultivar are similar to plants of the male parent variety, 'MZ-617' in most horticultural characteristics, however plants of the new cultivar have a different type of inflorescence and a more persistent inflorescence than plants of the male parent variety.

In comparison to the commercially available variety 'Gedi YP' (U.S. Plant Pat. No. 11,238), 'Moza Sunc 02' has a wider inflorescence diameter, more ray florets per inflorescence, fewer inflorescences per flowering branch, and the plants are shorter and more compact.

BRIEF DESCRIPTION OF THE PHOTOGRAPH

The photograph shows a plant of 'Moza Sunc 02' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The growing temperature ranged from 55° to 68° F. at night to 60° to 75° F. during the day. Measurements and numerical values represent averages of typical flowering types.

Botanical classification: *Dendranthema morifolium* cultivar 'Moza Sunc 02'.
Commercial classification: Garden-type Chrysanthemum.
Parentage: Hybridization of a female parent Chrysanthemum plant variety, 'MZ-923' (undistributed in the United States), and a male parent Chrysanthemum plant variety 'MZ-617' (undistributed in the United States).

PROPAGATION

Time to rooting: 7 to 14 days at approximately 21° C.
Rooting habit: Fine, fibrous.

PLANT

Growth habit: Mounding herbaceous perennial.
Height: Approximately 12.2 cm.
Spread: Approximately 12.5 cm.
Growth rate: Moderate.
Branching characteristics: Free Branching.
Length of lateral branches: Approximately 11.1 cm.
Number of leaves per lateral branch: Approximately 47.

FOLIAGE

Leaf:
- *Arrangement.*—Alternate.
- *Average length.*—Approximately 4.3 cm.
- *Average width.*—Approximately 3.8 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 138B. Mature foliage upper side: Near 137A. Mature foliage under side: Near 138B. Venation upper side: Near 145B. Venation under side: Near 138C.
- *Type.*—Net.

Petiole:
- *Average length.*—Approximately 2.8 cm.
- *Color.*—Near 137A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Daisy.
- *Natural flowering season.*—Approximately the middle two weeks of September.
- *Number of inflorescences per lateral branch.*—Approximately 13.
- *Inflorescence diameter.*—Approximately 4.3 cm.
- *Inflorescence depth.*—Approximately 1.1 cm.
- *Inflorescence longevity on plant.*—Approximately 17 days.
- *Persistence.*—Persistent.
- *Disc diameter.*—Approximately 1.4 cm.

Ray florets:
- *Appearance.*—Matte.
- *Texture.*—Smooth.
- *Average number per flower.*—56.
- *Shape.*—Obovate.
- *Aspect.*—Flat.
- *Margin.*—Entire.
- *Apex.*—Retuse.
- *Length.*—Approximately 1.3 cm.
- *Width.*—Approximately 0.5 cm.
- *Color.*—Upper surface at first opening: Near 4A. Upper surface at maturity: Near 3B. Upper surface at fading: Near 3B. Under surface at first opening: Near 4B. Under surface at maturity: Near 3C. Under surface at fading: Near 3C.

Disc florets:
- *Appearance.*—Shiny.
- *Texture.*—Smooth.
- *Average number per flower.*—Approximately 150.
- *Shape.*—Cylindrical.
- *Apex.*—Obtuse.
- *Average length.*—Approximately 0.4 cm.
- *Average width.*—Approximately 0.1 cm.
- *Color.*—At first opening: Near 154A. At maturity: Near 7A. At fading: Near 6A.

Peduncle:
- *Length.*—At terminal end (shortest): Approximately 2.4 cm. At lateral end (longest): Approximately 5.6 cm.
- *Angle to stem.*—Acute.
- *Strength.*—Moderate.
- *Color.*—Near 144A.
- *Habit.*—Upright.
- *Diameter.*—Approximately 0.2 cm.

Inflorescence bud:
- *Length.*—Approximately 0.6 cm.
- *Diameter.*—Approximately 0.9 cm.
- *Form.*—Globular.
- *Color.*—Near 154B.

Involucral bracts (phyllaries):
- *Appearance.*—Matte.
- *Texture.*—Lightly pubescent.
- *Number.*—Approximately 31.
- *Shape.*—Oblanceolate.
- *Margin.*—Entire.
- *Apex.*—Acute.
- *Length.*—Approximately 0.7 cm.
- *Width.*—Approximately 0.3 cm.
- *Color.*—Upper side: Near 144A. Under side: Near 144A.

REPRODUCTIVE ORGANS

Ray florets:
- *Pistillate.*—Number of pistils per flower: 1. Stigma shape: 2 branched. Stigma color: Near 5A. Style color: Near 154D. Style length: Approximately 0.5 cm.

Disc florets (hermaphroditic disc florets):
- *Pistillate.*—Number of pistils per flower: 1. Stigma shape: Two-branched. Stigma color: Near 3B. Style length: Approximately 0.4 cm. Style color: Near 2D.
- *Staminate.*—Number of stamens per flower: 5. Anther shape: Tubular. Anther color: Near 25B.
- *Pollen.*—No pollen detected.

What is claimed is:

1. A new and distinct cultivar of Chrysanthemum plant named 'Moza Sunc 02' as herein illustrated and described.

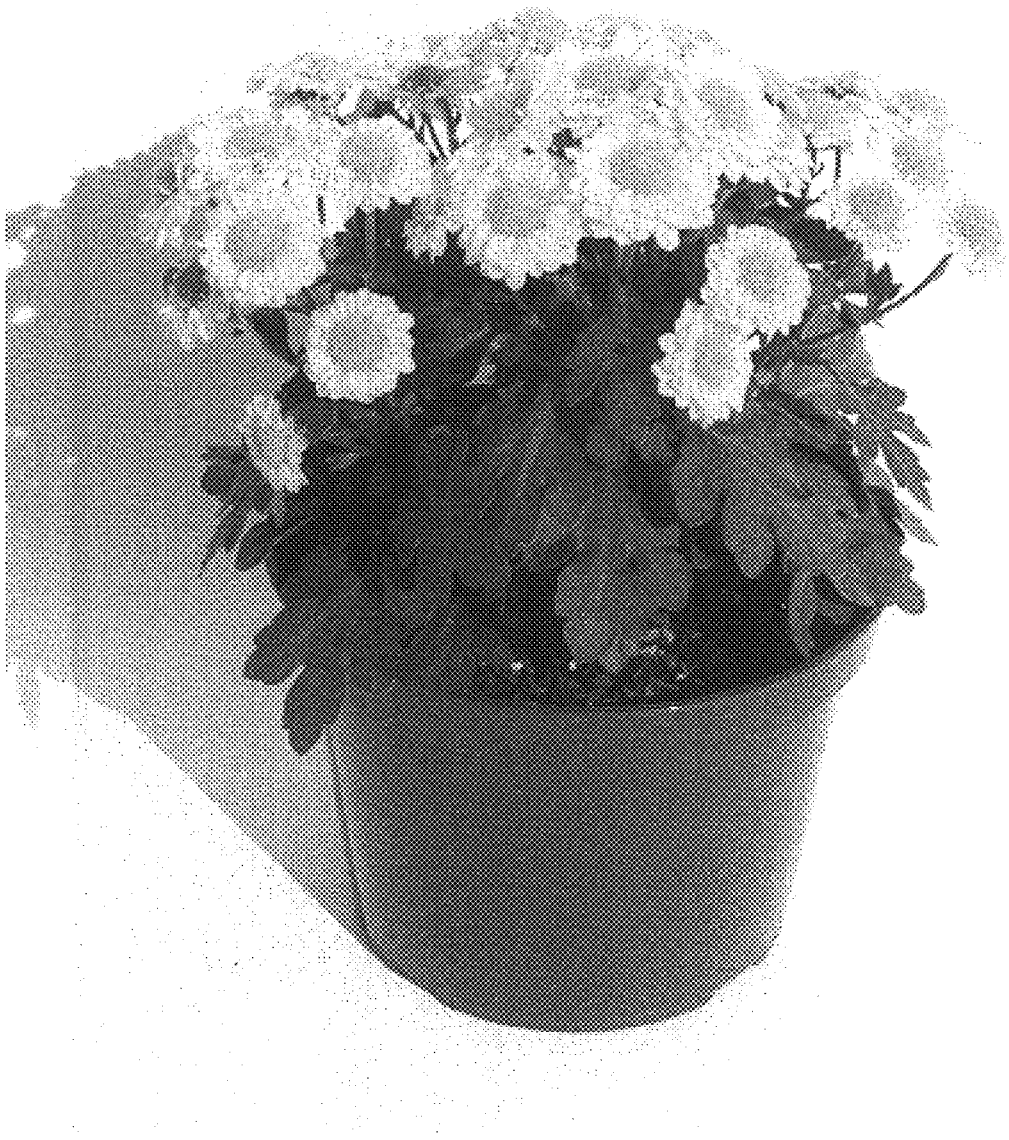

* * * * *